United States Patent [19]

Klainer et al.

[11] Patent Number: 4,960,408

[45] Date of Patent: Oct. 2, 1990

[54] TREATMENT METHODS AND VACCINES FOR STIMULATING AN IMMUNOLOGICAL RESPONSE AGAINST RETROVIRUSES

[76] Inventors: Albert S. Klainer, 315 W. 70th St., New York, N.Y. 10023; Emil Bisaccia, 4 Sunnybrook Rd., Basking Ridge, N.J. 07920

[21] Appl. No.: 295,454

[22] Filed: Jan. 10, 1989

[51] Int. Cl.$^5$ ............ A61M 37/00; A61N 1/30; A61K 41/00
[52] U.S. Cl. ............ 604/4; 604/20; 424/90
[58] Field of Search ............ 604/4-6, 604/20; 424/90; 210/927

[56] References Cited

U.S. PATENT DOCUMENTS

| | | | |
|---|---|---|---|
| 3,259,546 | 7/1966 | Polley | 167/78 |
| 3,462,526 | 8/1969 | Ratuld et al. | 424/90 |
| 3,660,234 | 5/1972 | Gray | 195/1.2 |
| 4,321,919 | 3/1982 | Edelson | 128/214 |
| 4,398,906 | 8/1983 | Edelson | 604/6 |
| 4,428,744 | 1/1984 | Edelson | 604/6 |
| 4,464,166 | 8/1984 | Edelson | 604/6 |
| 4,467,206 | 8/1984 | Taylor et al. | 250/435 |
| 4,522,810 | 6/1985 | Pedersen | 424/89 |
| 4,545,987 | 10/1985 | Giles et al. | 424/89 |
| 4,556,556 | 12/1985 | Wiesehahn et al. | 424/89 |
| 4,568,328 | 2/1986 | King | 604/6 |
| 4,568,542 | 2/1986 | Kronenberg | 424/90 |
| 4,573,960 | 3/1986 | Goss | 604/6 |
| 4,578,056 | 5/1986 | King et al. | 604/6 |
| 4,612,007 | 9/1986 | Edelson | 604/5 |
| 4,613,322 | 9/1986 | Edelson | 604/6 |
| 4,683,889 | 8/1987 | Edelson | 128/395 |
| 4,684,521 | 8/1987 | Edelson | 424/101 |
| 4,693,981 | 9/1987 | Wiesehahn et al. | 435/238 |
| 4,727,027 | 2/1988 | Wiesehahn | 435/173 |
| 4,748,120 | 5/1988 | Wiesehahn | 435/173 |
| 4,775,625 | 10/1988 | Sieber | 435/238 |
| 4,787,883 | 11/1988 | Kroyer | 604/4 |
| 4,791,062 | 12/1988 | Wiesehahn et al. | 435/238 |
| 4,824,432 | 4/1989 | Skurkovich et al. | 604/4 |
| 4,831,268 | 5/1989 | Fisch et al. | 250/432 R |
| 4,838,852 | 6/1989 | Edelson et al. | 604/4 |

OTHER PUBLICATIONS

Edelson, "Light-Activated Drugs", Scientific American, vol. 259, pp. 68-75, (reprint page Nos. 1-8), (1988).
Quinnan et al., "Inactivation of Human T-Cell Lymphotrophic Virus . . . ", Transfusion, vol. 26, pp. 481-483, (1986).
Hanson et al., "Photochemical Inactivation . . . ", J. Gen. Virol., vol. 40, pp. 345-358, (1978).
Nakashima et al., "Inactivation of Influenza . . . ", J. Virol., vol. 32, pp. 838-844, (1979).
"Principles and Practices of Infectious Diseases", 3rd. Ed., Mandell et al., Churchill Livingstone, New York, N.Y., pp. 2320-2334, (1990).
Dagleish et al., "Anti-Idiotypic Antibodies . . . ", Vaccine, vol. 6, pp. 215-220, (1988).
Shearer et al., "Importance of CD8+ T Helper Cell Function in AIDS", J. Inf. Dis., vol. 158, p. 893, (1988).
Buller et al., "Induction of Cytotoxic T-Cell Responses In vivo . . . ", Nature, vol. 328, pp. 77-79, (1987).
Murray et al., "Progression to AIDS . . . ", Am. J. Med., vol. 86, pp. 533-538, (1989).
NIH Conference, "Development and Evaluation of a Vaccine . . . ", Annals, Internal Med., vol. 110, pp. 373-385, (Mar. 1, 1989).
Fradd et al., "AIDS Vaccines: An Investor's Guide", Shearson, Lehman, Hutton, pp. 1-26, (Jun. 1, 1989).

*Primary Examiner*—C. Fred Rosenbaum
*Assistant Examiner*—Sharon Rose
*Attorney, Agent, or Firm*—Cohen, Pontani & Lieberman

[57] ABSTRACT

Human Immunodeficiency Virus infections, particularly AIDS, are treated by administering a psoralen compound which is subsequently activated by exposure to electromagnetic radiation (e.g. UVA light) whereby the activated psoralen compound attacks free virus and/or virus infected cells in the blood of the patient. The treated blood when presented to the patient's immune system engenders an effective immune response against the infection. The method has particular utility in the treatment of ARC patients who have depressed immune function.

21 Claims, No Drawings

TREATMENT METHODS AND VACCINES FOR STIMULATING AN IMMUNOLOGICAL RESPONSE AGAINST RETROVIRUSES

FIELD OF THE INVENTION

The present invention relates to the treatment of patients who are infected with a retrovirus, particularly the HIV retrovirus by using photopheresis in combination with the administration of a photoactive compound such as 8-methoxypsoralen. The invention also relates to vaccines against retroviruses, particularly the HIV retrovirus, and methods for producing said vaccines.

BACKGROUND OF THE INVENTION

Retroviruses form a sub-group of RNA viruses which, in order to replicate, must first reverse transcribe the RNA of their genome into DNA ("transcription" conventionally describes the synthesis of RNA from DNA). Once in the form of DNA, the viral genome is incorporated into the host cell genome, allowing it to take full advantage of the host cell's transcription/translation machinery for the purpose of replication. Once incorporated, the viral DNA is virtually indistinguishable from the host's DNA and, in this state, the virus may persist for as long as the cell lives.

A particular species of retrovirus has been isolated from patients who suffer from Acquired Immune Deficiency Syndrome (AIDS) and has been given the designation Human Immuno Deficiency Virus (HIV). This retrovirus will infect and destroy cells expressing the $CD^4$ marker and will preferentially infect and contribute to the destruction of human T-lymphocytes, commonly referred to as T-cells, bearing this marker which are involved in the functioning of the immune system. The patient progressively loses this set of T-cells, upsetting the overall balance of the immune system, reducing the patient's ability to combat other infections, and predisposing the patient to opportunistic infections which frequently prove fatal.

There are at least three clinical manifestations of HIV infection. In the initial "carrier" state, the only indication of infection is either the presence of HIV antibodies in the blood-stream or the ability to culture the virus. The next stage is known as 'AIDS related complex' (ARC) and the physical symptoms associated therewith may include persistent general lymphadenopathy, general malaise, increased temperature and chronic infections. This condition usually progresses to the final, fatal AIDS condition, when the patient loses the ability to fight infection.

A particularly troublesome problem associated with combatting the HIV retrovirus is that the RNA to DNA reverse transcription process is fraught with repeated mutation which makes it extremely difficult for the body's immune system to recognize and attack infected cells along with the virus itself.

It is therefore, an object of this invention to provide a treatment for patients infected with a retrovirus, particularly the HIV retrovirus. It is a further object of the invention to enhance the body's ability to recognize and attack T-cells which are infected with the HIV retrovirus.

It is also an object of the invention to increase the number of T-cells in patients infected with HIV who have low numbers of T-cells due to the HIV infection and the patient's accompanying immunologic response.

A still further object of the invention is to provide a vaccine against infection by a retrovirus, particularly the HIV retrovirus.

Other objects of the invention will be apparent from the description of the invention which follows.

BRIEF DESCRIPTION OF THE INVENTION

In accordance with the present invention a method has been found for treating patients who are infected with a retrovirus, such as the HIV retrovirus using a photoactive compound which is capable of binding to nucleic acids in infected nucleated cells of the patient upon activation by exposure to ultraviolet light. The photoactive compound (e.g. 8 methoxypsoralen) is administered to the patient's blood in vitro or in vivo using conventional administration routes.

A portion of the patient's blood is then treated (preferably, extracorporeally) using photopheresis, which comprises subjecting the blood to ultraviolet light, preferably long wavelength ultraviolet light in the wavelength range of 320 to 400 nm, commonly called UVA light. The treated blood, or a fraction thereof, is returned to the patient (in the case of extracorporeal photopheresis) or remains in the patient (following in vivo photopheresis) to stimulate an immunological response by the patient's immune system against the infected cell population and/or against the retrovirus to inhibit progression of the retroviral infection.

Vaccines against retroviruses and methods of making same are also provided according to the invention. According to the invention, a photoactive compound (as described above) is administered to the blood of a donor who is infected with a retrovirus, such as the HIV retrovirus and/or who is diagnosed as suffering from AIDS or AIDS Related Complex. At least a portion of the donor's blood is then treated using photopheresis, as described above. The treated blood or some fraction thereof may be used as a vaccine.

Optionally, the treated blood, or a fraction thereof, is processed by conventional techniques to substantially remove the erhythrocytes. The resulting processed fraction is then used as a vaccine which can be administered to a patient as a type specific white blood cell transfusion.

Thus, the invention also provides vaccines, which may be made as described above, against retroviruses, such as HIV.

DETAILED DESCRIPTION OF THE INVENTION

The present invention is directed to the use of photopheresis to attenuate retroviruses and/or kill blood cells which have been infected with a retrovirus. While it is not intended that the scope of the present invention be limited by any specific theory of operation, it is believed that retrovirus infections which are not controlled by the normal immunological response of a patient can be treated by damaging infected nucleated blood cells (such as T cells) using a photopheresis treatment according to the invention. The treated cells as well as killed and/or attenuated retrovirus, peptides, native subunits of the retrovirus itself (which are released upon cell break-up and/or shed into the blood) and/or pathogenic noninfectious retroviruses are then used to generate an immune response.

While the treatment methods according to the present invention can be applied to the treatment of any retrovirus infection, they are particularly useful in the treatment of HIV infection.

According to the claimed methods, a photoactive compound is first administered to the blood of a patient who is infected with a retrovirus of a type which attacks nucleated blood cells. The photoactive compound may be administered in vivo (e.g. orally or intravenously) or may be administered in vitro to a portion of the patient's blood which has been removed from the patient by employing conventional blood withdrawal techniques.

In accordance with the present invention, the photoactive compound should be capable of binding to nucleic acids upon activation by exposure to electromagnetic radiation of a prescribed spectrum, e.g., ultraviolet light.

Next, the portion of the patient's blood to which the photoactive compound has been administered is treated by subjecting the portion of the blood to photopheresis using ultraviolet light. The photopheresis step is preferably carried out in vitro using an extracorporeal photopheresis apparatus. The photopheresis step in accordance with the present invention may also be carried out in vivo. A presently preferred extracorporeal photopheresis apparatus for use in the methods according to the invention is currently manufactured by Therakos, Inc., Westchester, Pa. under the name UVAR. A description of such an apparatus may be found in U.S. Pat. No. 4,683,889, granted to R.L. Edelson on Aug. 14, 1987, the contents of which are hereby incorporated by reference in their entirety. The exposure of blood to ultraviolet light in a photopheresis apparatus is within the ability of persons having ordinary skill in the art.

When the photopheresis step is carried out in vitro, at least a fraction of the treated blood is returned to the patient following the photopheresis treatment to stimulate the patient's immune response to the infected cell population and to the retrovirus itself. Preferably, the treatment method described hereinabove is repeated at an interval of about once per week to about once every four weeks.

Preferred photoactive compounds for use in accordance with the present invention are compounds known as psoralens (or furocoumarins) which are described in U.S. Pat. No. 4,321,919 the disclosure of which is incorporated herein by reference.

The preferred photoactive compounds for use in accordance with the present invention include the following:
psoralen;
8-methoxypsoralen;
4,5'8-trimethylpsoralen;
5-methoxypsoralen;
4-methylpsoralen;
4,4-dimethylpsoralen;
4-5'-dimethylpsoralen; and
4',8-methoxypsoralen The most particularly preferred photoactive compound for use in accordance with the invention is 8-methoxypsoralen.

The photoactive compound, when administered to the patient's blood in vivo is preferably administered orally, but also can be administered intravenously and/or by other conventional administration routes.

The preferred dosage of the photoactive compound is in the range of about 0.3 to about 0.7 mg/kg. most preferably about 0.6 mg/kg.

When administered orally, the photoactive compound should preferably be administered at least about one hour prior to the photopheresis treatment and no more than about three hours prior to the photopheresis treatment. If administered intravenously, the times would be shorter.

The photopheresis treatment in the treatment methods according to the invention is preferably carried out using long wavelength ultraviolet light (UVA) at a wavelength within the range of 320 to 400 nm. The exposure to ultraviolet light during the photopheresis treatment preferably has a duration of about three to four hours, although shorter or longer treatment periods may be used if desired.

When the photopheresis treatment according to the invention is carried out in vivo, careful attention should be paid to controlling the maximum radiant exposure so as to avoid unnecessary injury to the patient. Methods for calculating maximum radiant exposure to ultraviolet light are known in the art and, therefore, shall not be described herein.

The invention also provides methods for making retrovirus vaccines. According to the invention, a donor who is infected with a retrovirus, such as HIV may be utilized to produce a vaccine against his retrovirus infection as follows.

First, a photoactive compound as described hereinabove is administered to at least a portion of the donor's blood either prior to removal of the blood, either orally or intravenously, or after removal from the patient in which case it is administered in vitro. Optionally, a portion of the donor's blood could first be processed using known methods to substantially remove the erhythrocytes and the photoactive compound is then administered to the resulting enriched leukocyte fraction.

In any case, the portion of blood (or enriched leukocyte fraction thereof) to which the photoactive compound has been administered is subjected to a photopheresis treatment using ultraviolet light, preferably UVA in the manner previously described. The treated blood or the treated enriched leukocyte fraction (as the case may be) is then administered back to the donor as an autogenous vaccine.

Alternatively, as is within the ability of persons having ordinary skill in the art, the treated portion of blood from the donor can be administered to another person in need of vaccination against the retrovirus. Preferably, however, the treated portion of blood from the donor is processed using known methods to substantially remove the erhythrocytes and, optionally, to reduce white cell antigenicity either prior to the photopheresis treatment, as described above, or after the photopheresis treatment. Removal of the erhythrocytes from the blood yields a leukocyte enriched fraction which can be administered to a patient, who is in need of vaccination against the retrovirus, as a type specific white blood cell transfusion.

Additionally, in accordance with the present invention, the treated enriched leukocyte fraction, which is itself a mixture of various blood components including peptides or polypeptides, eg., cytokines, lymphokines, monokines, etc., and/or the treated portion of blood may be processed, as is within the ability of persons having ordinary skill in the art, to isolate a particular component or components which may be used in the treatment of the retrovirus infection of the donor and/or may be used as a vaccine against the retrovirus.

EXAMPLE

A male patient, 39 years of age, weighing approximately 70 kg and who had been diagnosed as having AIDS Related Complex, was treated in accordance with the present invention as follows:

8-methoxypsoralen was administered orally to the patient during the afternoon of the first day of treatment at a dosage of 30 mg (i.e. about 0.4 mg/kg). Approximately one hour after the 8-methoxypsoralen had been administered to the patient he was prepared for withdrawal of a portion of his blood for photopheresis treatment using a Therakos UVAR photopheresis machine.

A centrifuge which is integral with the photopheresis machine was used to spin off substantially all of the erhythrocytes from the withdrawn blood and these were subsequently returned to the patient. Next, approximately 300cc of plasma and 240cc of buffy coat (which includes the Tlymphocytes) were removed in six cycles (40cc of buffy coat per cycle). The buffy coat and plasma were subjected to UVA light exposure beginning after 40cc of buffy coat had been collected in the first cycle. The irradiation was continued through all six cycles and then for an additional one and one-half hours for a total irradiation time of approximately four hours. The irradiated buffy coat and plasma were then returned to the patient. This process was repeated in the morning of the following day.

The blood parameters of the patient before receiving the photopheresis treatment according to the invention and five weeks after receiving the treatment are set forth in Table I.

TABLE I
Blood Parameters of ARC Patient Treated By The Photopheresis Method According To The Invention

| Blood Parameter | Before Treatment | After Treatment | Normal Range |
|---|---|---|---|
| HEMOGLOBIN | 11.7 G/DL | 10.8 G/DL | — |
| HEMACRIT | 33.9% | 33.6% | — |
| WBC | 5.2 /UL | 4.7 /UL | — |
| WBC DIFFERENTIAL: | | | |
| Bands | 16% | 16% | — |
| Seg. Neut. | 29% | 23% | — |
| Lymphocytes | 43% | 46% | — |
| Atyp. Lymph. | 7% | 7% | — |
| Monocytes | 5% | 6% | — |
| PLATELETS | 208,000 | 241,000 | — |
| LYMPHOCYTES: | | | |
| $CD^3$ ($T^3$) | 17% | 85% | 56–78% |
| $CD^4$ ($T^4$) | 4% | 22% | 32–50% |
| $CD^8$ ($T^8$) | 26% | 62% | 13–38% |
| $T^4/T^8$ RATIO | 0.15 | 0.4 | 0.8–1.9 |

It should be understood that while the foregoing description has been provided to illustrate the present inventions, it is not intended to limit the scope of the inventions as various modifications to the inventions described herein may be made by persons having ordinary skill in the art without departing from the spirit and scope thereof as defined in the following claims.

We claim:

1. A method for treating a patient having an HIV retrovirus infection, said method comprising the steps of:
   a. administering to an infected patient's blood a psoralen compound; and
   b. treating at least a portion of the patient's blood to which the psoralen compound has been administered, said treatment comprising subjecting the portion of blood to photopheresis using electro-magnetic radiation of a spectrum which activates the psoralen compound, whereby the activated psoralen compound reacts with the HIV retrovirus and/or HIV retrovirus infected cells in the portion of blood undergoing photopheresis, the psoralen compound and electro-magnetic radiation being administered in doses which are effective for controlling the infection.

2. The method of claim 1, wherein the administration of the psoralen compound is performed in vitro.

3. The method of claim 1, wherein the administration of the psoralen compound is performed in vivo.

4. The method of claim 2, wherein the step (b) is conducted extracorporeally and wherein said method further comprises the step of returning the treated portion of blood to the patient following step (b).

5. The method of claim 3, wherein the step (b) is conducted extracorporeally and wherein said method further comprises the step of returning the treated portion of the blood to the patient following step (b).

6. The method of claim 1, wherein the electro-magnetic radiation is ultraviolet light.

7. The method of claim 6, wherein the psoralen compound is selected from the group consisting of, psoralen, 8-methoxypsoralen, 4,5', 8-trimethylpsoralen, 5-methoxypsoralen, 4methylpsoralen, 4,4-dimethylpsoralen, 4,5'-dimethylpsoralen, and 4', 8-dimethylpsoralen.

8. The method of claim 7, wherein the psoralen compound is selected from the group consisting of 8-methoxypsoralen, psoralen and 4,5',8-trimethylpsoralen.

9. The method of claim 8, wherein the psoralen compound is 8-methoxypsoralen.

10. The method of claim 9, wherein the 8-methoxypsoralen is administered in a dosage of at least about 0.6 mg/kg.

11. The method of claim 10, wherein the 8-methoxypsoralen is administered orally.

12. The method of claim 10, wherein the 8-methoxypsoralen is administered intravenously.

13. The method of claim 9, wherein steps (a) and (b) are carried out twice, once on each of two successive days, said two day treatment being repeated at an interval of between about one to four weeks.

14. The method of claim 10, wherein steps (a) and (b) are carried out twice, once on each of two successive days, said two day treatment being repeated at an interval of between about one to four weeks.

15. A method for treating an infected patient who has been diagnosed as either being in AIDS carrier or who has AIDS or AIDS Related Complex, said method comprising the steps of:
   a. administering 8-methoxypsoralen to at least a portion of the infected patient's leukocytes;
   b. then subjecting at least a portion of the infected patient's leukocytes to which the 8-methoxypsoralen has been administered to extracorporeal photopheresis using UVA light, whereby the 8-methoxypsoralen is activated and reacts with the infected patient's leukocytes in the portion thereof undergoing photopheresis; and
   c. infusing the leukocytes treated in steps (a) and (b) back into the patient, wherein the 8-methoxypsoralen and UVA light are administered in doses which are effective for controlling the infection.

16. The method of claim 15, wherein the dosage of 8-methoxypsoralen which is used in step (a) is about 0.6 mg/kg administered orally to the infected patient no more than about 3 hours prior to photopheresis.

17. The method of claim 15, wherein the 8-methoxypsoralen used in step (a) is administered intravenously to an enriched fraction of the infected patient's leukocytes at a dosage which is equivalent to about 0.6 mg/kg and is administered no more than about 3 hours prior to photopheresis.

18. A method for treating an infected patient who has been diagnosed as an AIDS carrier or who has AIDS or AIDS Related Complex, said method comprising the steps of:
   a. administering to the infected patient's leukocytes a psoralen compound; and
   b. then treating at least a portion of the infected patient's leulocytes to which the psoralen compound has been administered by subjecting the portion of leukocytes to photopheresis using ultraviolet light, whereby the psoralen compound is activated and reacts with the infected leukocytes undergoing photopheresis, the psoralen compound and ultraviolet light being administered in doses which are effective for controlling the infection.

19. The method of claim 18, wherein the psoralen compound is 8-methoxypsoralen.

20. A method for increasing the number of a patient's non-infected $CD^4$ lymphocytes in a patient suffering from an abnormally low number of $CD^4$ lymphocytes due to a retrovirus infection, such as an HIV infection, said method comprising the steps of:
   a. administering 8-methoxypsoralen to at least a portion of the patient's infected $CD^4$ lymphocytes in a dosage range of about 0.3–0.7 mg/kg; and
   b. then exposing at least a fraction of the portion of infected $CD^4$ lymphocytes to UVA light.

21. The method of claim 20 wherein the dosage of 8-methoxypsoralen is about 0.6 mg/kg.

* * * * *